United States Patent
Park et al.

(10) Patent No.: US 11,452,682 B2
(45) Date of Patent: Sep. 27, 2022

(54) TOOTHPASTE COMPOSITION FOR ALLEVIATING DENTIN HYPERESTHESIA

(71) Applicant: HYSENSBIO, Gwacheon-si (KR)

(72) Inventors: Joo Hwang Park, Incheon (KR); Ji Hyun Lee, Seoul (KR)

(73) Assignee: HYSENSBIO, Gwacheon (KR)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 17/053,404

(22) PCT Filed: Apr. 17, 2019

(86) PCT No.: PCT/KR2019/004636
§ 371 (c)(1),
(2) Date: Nov. 6, 2020

(87) PCT Pub. No.: WO2019/216568
PCT Pub. Date: Nov. 14, 2019

(65) Prior Publication Data
US 2021/0369584 A1    Dec. 2, 2021

(30) Foreign Application Priority Data

May 9, 2018 (KR) .................. 10-2018-0053013

(51) Int. Cl.
*A61K 8/64* (2006.01)
*A61K 8/24* (2006.01)
*A61Q 11/00* (2006.01)

(52) U.S. Cl.
CPC .................. *A61K 8/64* (2013.01); *A61K 8/24* (2013.01); *A61Q 11/00* (2013.01)

(58) Field of Classification Search
CPC ................................ A61K 8/64; A61K 47/62
USPC .............................................. 514/23; 424/79
IPC ................................... A61Q 11/00; C07K 7/06
See application file for complete search history.

(56) References Cited

U.S. PATENT DOCUMENTS

| | | | | |
|---|---|---|---|---|
| 5,624,906 A | * | 4/1997 | Vermeer .................. | A61K 8/60 514/23 |
| 8,557,224 B2 | | 10/2013 | Yamagishi et al. | |
| 2003/0152525 A1 | | 8/2003 | Dixon, Jr. et al. | |
| 2010/0330002 A1 | | 12/2010 | Robinson et al. | |
| 2011/0020246 A1 | * | 1/2011 | Strand ...................... | A61K 8/21 424/52 |
| 2017/0189287 A1 | | 7/2017 | Itakura et al. | |
| 2021/0154123 A1 | | 5/2021 | Park et al. | |

FOREIGN PATENT DOCUMENTS

| | | | |
|---|---|---|---|
| CN | 106456485 A | 2/2017 | |
| ER | 2934443 B1 | 9/2017 | |
| ER | 3733686 A1 | 11/2020 | |
| JP | 10-17449 A | 1/1998 | |
| JP | 2003160457 A | 6/2003 | |
| JP | 2015-524466 A | 8/2015 | |
| KR | 10-2010-0039750 A | 4/2010 | |
| KR | 10-2014-0021142 A | 2/2014 | |
| KR | 10-2017-0045246 A | 4/2017 | |
| KR | 10-1772449 B1 | 8/2017 | |
| KR | 101772449 * | 9/2017 | ............... A61K 8/64 |
| KR | 10-1956578 B1 | 3/2019 | |
| KR | 10-1956579 B1 | 3/2019 | |
| RU | 2337734 C2 | 11/2008 | |
| RU | 2 467 739 C1 | 11/2012 | |
| RU | 2 477 122 C2 | 3/2013 | |
| WO | 2016/114137 A1 | 7/2016 | |
| WO | 2017/072105 A1 | 5/2017 | |
| WO | 2017/123986 A1 | 7/2017 | |

OTHER PUBLICATIONS

International Search Report for PCT/KR2019/004636 dated Aug. 1, 2019 (PCT/ISA/210).
Extended European Search Report dated Apr. 8, 2022 from the European Patent Office in EP Application No. 19800686.8.
"Breathaway Mouth Rinse Fresh Mint", <URL:https://dailymed.nlm.nih.gov/dailymed/drugInfo.cfm?setid=37b2c031-ecc9-4420-9d84-e71c0e529187>, U.S. National Library of Medicine, Feb. 2018 (9 pages total).
Isabel C. C. M. Porto et al., "Diagnosis and treatment of dentinal hypersensitivity", Journal of Oral Science, 2009, pp. 323-332, vol. 51, No. 3 (10 pages total).
International Search Report for PCT/KR2019/004635 dated Jul. 25, 2019 [PCT/ISA/210].
Extended European Search Report dated Mar. 18, 2022 from the European Patent Office in EP Application No. 19799399.1.

* cited by examiner

*Primary Examiner* — Walter E Webb
(74) *Attorney, Agent, or Firm* — Sughrue Mion, PLLC

(57) ABSTRACT

A toothpaste composition for alleviating dentin hyperesthesia is disclosed. The composition includes a peptide consisting of an amino acid sequence of the following Formula 1:

K-Y-R1-R2-R3-R4-R5-R6-R7-R8    (Formula 1)

wherein R1 is arginine (R), lysine (K) or glutamine (Q);
R2 is arginine (R) or glutamine (Q);
R3, R4, and R5 are arginine (R) or lysine (K), respectively;
R6 is asparagine (N) or serine (S); and
R7 and R8 are lysine (K) or tyrosine (Y), respectively.

8 Claims, 7 Drawing Sheets
Specification includes a Sequence Listing.

Comparative test example 3-1

Comparative test example 3-2

Test example 3

TOOTHPASTE COMPOSITION FOR ALLEVIATING DENTIN HYPERESTHESIA

CROSS REFERENCE TO RELATED APPLICATIONS

This application is a National Stage of International Application No. PCT/KR2019/004636 filed Apr. 17, 2019, claiming priority based on Korean Patent Application No. 10-2018-0053013 filed May 9, 2018.

BACKGROUND OF THE INVENTION

1. Field of the Invention

The present invention relates to toothpaste composition, and more specifically, the present invention relates to toothpaste composition for preventing or alleviating dentin hyperesthesia by inducing physiological remineralization of defects in dentin constituting a tooth.

2. Description of the Related Art

Dentin hyperesthesia, commonly referred to as 'sensitive dentin', is a common symptom experienced by 8% to 57% of the adult population. In particular, the case of periodontal disease, which is the most common disease in Korea, 72.5% to 98% of patients suffer from 'sensitive dentin' (Source: National Health Information Portal Medical Information; health.cdc.go.kr/health/Main.do).

Dentin hyperesthesia can be defined as a pain caused by the exposure of dentinal tubules transmitting all external stimuli to the pulp nerve. This makes the pulp nerve to be more sensitive to the same stimulus. Although there are no nerves in the dentin itself, but we can perceive the changes because the cold temperature stimulus is transmitted through the dentinal tubules to the nerves inside the pulp.

In the dentin, which occupies the most part of the tooth, there are dentinal tubules that extend from the pulp to the enamel. These tubules are filled with liquid. The diameter increases toward the pulp and has a dense structure. Because of these distinct structures, external stimuli can be transmitted quickly to the pulp nerve. If the dentin surface is damaged and the number of exposed dentinal tubules increases, it may cause a more sensitive reaction to the same stimulus than usual.

Currently, there are two ways for dentin hyperesthesia, depending on the principle of action. One is to interfere with the signal transmission of the nerve that transmits pain, and the other is to block the exposed dentinal tubules to alleviate the symptoms.

Dipotassium phosphate ($K_2HPO_4$) has been widely used in a method for interfering with the signal transmission of nerves that transmit pain. However, dipotassium phosphate has a low pain-blocking effect and must be used repeatedly, and it is not an effective treatment method because it limits the sense of chewing.

Next, calcium hydrogen phosphate ($CaHPO_4$), fluorine, oxalate, arginine (amino acid), and calcium carbonate ($CaCO_3$) are used to block the dentinal tubules. In recent years, considering the inconvenience of receiving treatment at the dentist for dentin hypersensitivity, toothpastes for preventing or alleviating dentin sensitivity are on the market, including calcium phosphate, dental type silica, strontium chloride, calcium carbonate or tricalcium phosphate, as active ingredients. However, these are also foreign materials different from the original dentin, so there would be a gap created in the peripheral boundary area between dentin and the foreign materials. The nerve would be exposed again after the foreign material being separated from the sealing, and it would cause a recurrence of dentin sensitivity.

SUMMARY OF THE INVENTION

Embodiments of the present inventive concepts may provide toothpaste composition for alleviating dentin hyperesthesia, comprising a peptide including an amino acid sequence of the following Formula 1:

K-Y-R1-R2-R3-R4-R5-R6-R7-R8 (Formula 1)

wherein R1 is arginine (R), lysine (K) or glutamine (Q);
R2 is arginine (R) or glutamine (Q);
R3, R4, and R5 are arginine (R) or lysine (K), respectively;
R6 is asparagine (N) or serine (S); and
R7 and R8 are lysine (K) or tyrosine (Y), respectively.

Embodiments of the present inventive concepts may also provide a composition for oral care comprising a peptide including any one amino acid sequence of SEQ ID NOS: 1 to 96.

Embodiments of the present inventive concepts, 0.0015-0.0025 parts by weight of the peptide may be included based on 100 parts by weight of the composition.

Embodiments of the present inventive concepts, 31.00-33.00 parts by weight of tricalcium phosphate may be included based on 100 parts by weight of the composition.

Embodiments of the present inventive concepts, 0.045-0.055 parts by weight of hydroxyapatite may be included based on 100 parts by weight of the composition.

Embodiments of the present inventive concepts, the toothpaste composition may include 20-22 parts by weight of purified water, humectant 33-37 parts by weight, viscosity modifier 4.4-5.4 parts by weight, surfactant 1.1-1.3 parts by weight, flavoring agent 0.8-0.9 parts by weight, and diluting agent 0.04-0.06 parts by weight based on 100 parts by weight of the composition.

Embodiments of the present inventive concepts, the toothpaste composition may include 0.15-0.25 parts by weight of aminocaproic acid and 1.9-2.1 parts by weight of allantoin based on 100 parts by weight of the composition.

Embodiments of the present inventive concepts, the humectant may be D-sorbitol solution or sodium PCA solution, or concentrated glycerin, the viscosity modifier may be hydrous silicic acid, xanthan gum or CMC(Carboxymethyl Cellulose Sodium Salt), the surfactant may be sodium cocoylmethyltaurate, flavoring agent is green tea extract, chamomile extract, rosemary extract, myrrh tincture, rhatany tincture, chamomile tincture, mastic oil 40 HF-60662, propolis extract, grapefruit seed extract, spearmint B71228 or peppermint oil 81689, and the diluting agent may be hydroxyapatite.

Embodiments of the present inventive concepts, the humectant may include 80-83% by weight of the D-sorbitol solution, 7-8% by weight of the Sodium PCA solution, and 10-12% by weight of the concentrated glycerin.

Embodiments of the present inventive concepts, the viscosity modifier may include 79-85% by weight of the hydrous silicic acid, 4-8% by weight of xanthan gum, and 11-13% by weight of the CMC.

Effect of the Invention

The present inventive concepts may provide toothpaste composition that prevents or alleviates dentin hyperesthesia by sealing off exposed defects of the dentinal tubule through physiological remineralization of dentin.

Other aspects, advantages and salient features of the embodiments will become apparent to those skilled in the art from the following detailed description, which, taken in conjunction with the annexed drawings, discloses exemplary embodiments of the disclosure.

BRIEF DESCRIPTION OF THE DRAWINGS

In FIG. 2, A shows the molecular weight of the peptide itself contained in the toothpaste composition for relieving dentin hyperesthesia according to an embodiment of the present invention. In FIG. 2, B shows the molecular weight of the peptide contained in the state of the toothpaste composition for relieving dentin hyperesthesia according to an embodiment of the present invention.

Figure 1A:
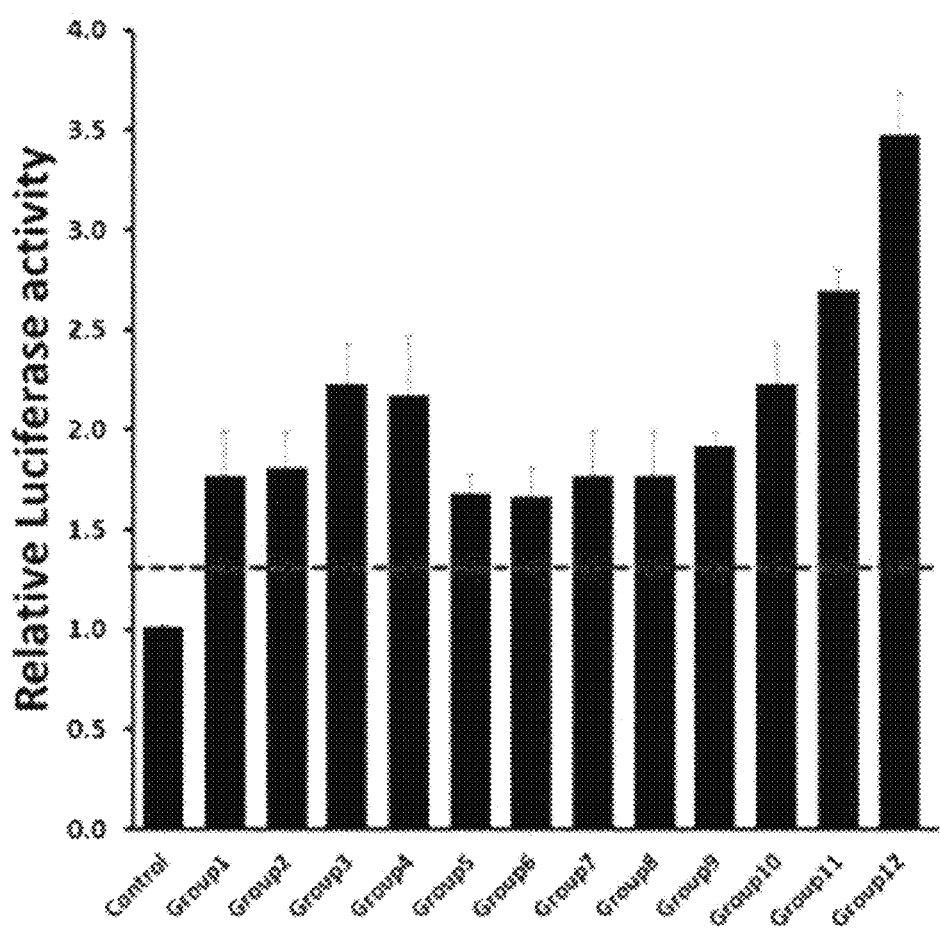
FIG. 1A is a graph showing the results of comparing the effect of the respective groups of the peptide included in the toothpaste composition for alleviating dentin hyperesthesia according to an embodiment of the present invention on the expression of DSPP, which is an odontoblast differentiation marker gene.

A-D shows the dentinal tubules treated only with purified water (comparative test example 3-1), E-H is showing the dentinal tubules brushed using a toothpaste composition without the peptide comparing with the embodiment of the present invention (comparative test example 3-2), and I-L shows the dentinal tubules brushed using a toothpaste composition for alleviating dentin hyperesthesia according to the embodiment of the present invention (scale bar: A, E, I, 100 μm; B, F, J, 20 μm; C, G, K, 20 μm; D, H, L, 10 μm). In each case, the dentin slices with exposed dentinal tubules were washed 3 times with distilled water after brushing once a day for 1 minute and then immersed in artificial saliva. After repeating this process for 2 weeks, the ability to seal off the dentin tubules was observed with a scanning electron microscope.

DETAILED DESCRIPTION OF THE PREFERRED EMBODIMENTS

Reference will now be made in detail to embodiments, examples of which are illustrated in the accompanying drawings, wherein like reference numerals refer to like elements throughout. In this regard, the present embodiments may have different forms and should not be construed as limited to the descriptions set forth herein. Unless otherwise defined, all terms including technical and scientific terms used herein have the same meaning as commonly understood by one of ordinary skills in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In addition, terms to be described later are defined in consideration of contributions in the present disclosures, which may vary according to the intention of the user or practice.

The disclosure now will be described more fully hereinafter with reference to the accompanying drawings, in which illustrative embodiments of the disclosure are shown. This disclosure may, however, be embodied in many different forms and should not be construed as limited to the embodiments set forth herein; rather, these embodiments are provided so that this disclosure will be thorough and complete and will fully convey the scope of the disclosure to those skilled in the art. However, as it is presented as an example, the present invention is not limited thereto and the present invention is defined only by the scope of the claims which will be described later.

It will be understood that the terms "comprises" and/or "comprising," when used in this specification, specify the presence of stated components, this means that it may contain more components, rather than exclude other components, unless there is a particularly contrary article.

Hereinafter, embodiments of the present invention are described in more detail.

An odontoblast may refer to a cell that synthesizes and secretes proteins and polysaccharides composing the matrix of the dentin. It is a columnar cell that is in contact with the predentin (uncalcified dentin) and forms a cell layer at the periphery of the dental pulp. It is a differentiated cell (becoming a cell derived from the mesenchymal ectoderm) involved in calcification of dentin. At the developmental stage, an odontoblast faces the enamel among the cells of the dental papilla, involved in calcification of dentin.

A peptide, included in the toothpaste composition for alleviating dentin hyperesthesia according to an embodiment of the present invention (hereinafter, 'odontoblast differentiation promoting peptide'), does not exhibit cytotoxicity, but it is possible to increase the expression level of the odontoblast differentiation marker genes DSPP, Dmp1 and Nestin. When transplanted in vivo with pulp tissue cells, the pulp tissue cells may form a dentin/dentin-like tissue.

Odontoblast differentiation promoting peptide includes mutant peptides having a sequence different from the amino acid sequence constituting the amino acid sequence and at least one amino acid residue, as long as it can promote dentin regeneration or treat dentin hyperesthesia.

Amino acid exchanges in proteins and polypeptides, which do not generally alter the molecular activity, are known in the art. The most commonly occurring exchanges are amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, Asp/Gly, in both directions. The peptide may include peptides that have improved structural stability against heat, pH, etc., or improved ability to promote regeneration of dentin or dental pulp due to alteration or modification of the amino acid sequence.

For example, although glutamine which is an acidic amino acid at position 3 of the peptide of SEQ ID NO: 1 of the present invention is substituted with a basic amino acid, lysine or arginine, the effects of the peptide of the present invention may be obtained as it is; although arginine which is a basic amino acid at position 4 or 5 of the peptide of SEQ ID NO: 1 is substituted with an acidic amino acid glutamine or a basic amino acid lysine, the effects of the peptide of the present invention may be obtained as it is; although lysine which is a basic amino acid at position 6, 7, or 9 of the peptide of SEQ ID NO: 1 is substituted with a basic amino acid arginine or an aromatic amino acid tyrosine, the effects of the peptide of the present invention may be obtained as it is; although asparagine which is an acidic amino acid at position 8 of the peptide of SEQ ID NO: 1 is substituted with a neutral amino acid serine, the effects of the peptide of the present invention may be obtained as it is; and although tyrosine which is an aromatic amino acid at position 10 of the peptide of SEQ ID NO: 1 is substituted with a basic amino acid lysine, the effects of the peptide of the present invention may be obtained as it is.

As such, although the acidic amino acids, basic amino acids, or aromatic amino acids constituting the peptide of the present invention are substituted with amino acids having the same properties, or substituted with different acidic amino acids, basic amino acids, neutral amino acids, or aromatic amino acids, respectively, the effects of the peptide of the present invention may be obtained as it is. Therefore, it is apparent that a peptide variant having a sequence including one or more amino acid residues different from those of the amino acid sequence constituting the peptide of the present invention is also included in the scope of the peptide of the present invention.

Further, although arbitrary amino acids are added at the N-terminus or C-terminus of the peptide of the prevention, the effects of the peptide of the present invention may be obtained as it is. Therefore, a peptide prepared by adding arbitrary amino acids at the N-terminus or C-terminus of the peptide of the present invention is also included in the scope of the peptide of the present invention. For example, a peptide prepared by adding 1 to 300 amino acids at the N-terminus or C-terminus of the peptide of the present invention may be exemplified, for another example, a peptide prepared by adding 1 to 100 amino acids at the N-terminus or C-terminus of the peptide of the present invention may be exemplified, and for still another example, a peptide prepared by adding 1 to 24 amino acids at the N-terminus or C-terminus of the peptide of the present invention may be exemplified.

The mRNA of the DSPP gene in MDPC-23 cells treated with the odontoblast differentiation promoting peptide, compared to the mRNA level of the DSPP gene in MDPC-23 cells (control) not treated with the odontoblast differentiation promoting peptide, was all 1.3 times or more (Tables 13 to 24).

As reported up to now, it is known that as the mRNA level of DSPP is increased, odontoblast differentiation and dentin regeneration are promoted, and therefore, it can be seen that 128 kinds of peptides increases the mRNA level of Dspp gene, which in turn may exhibit the effect of promoting odontoblast differentiation and dentin regeneration (Taduru Sreenath et al., THE JOURNAL OF BIOLOGICAL CHEMISTRY, Vol. 278, No. 27, Issue of July 4, pp. 24874-24880, 2003; William T. Butler et al., Connective Tissue Research, 44(Suppl. 1): 171-178, 2003).

The peptide included in the toothpaste composition for alleviating dentin hyperesthesia may be used in a single form of the peptide or a polypeptide form of 2 or more repeats of the peptide, and the peptide may also be used in a complex form of a drug having a therapeutic effect on dentin or dental pulp diseases linked at the N-terminus or C-terminus of the peptide.

Example 1

Synthesis of Peptides for Promoting Odontoblast Differentiation

The present inventors synthesized a peptide (SEQ ID NO: 1) showing the effect of promoting regeneration of dentin or dental pulp tissues by a 9-fluorenylmethyloxycarbonyl (Fmoc) method, and they synthesized peptides of respective groups (Tables 1 to 12) by substituting the amino acids of the synthesized peptide.

N-KYQRRKKNKY-C(SEQ ID NO: 1)

First, peptides of Group 1 were synthesized by using the peptide of SEQ ID NO: 1 or by substituting any amino acid at positions 5 to 7 of the peptide of SEQ ID NO: 1 with lysine or arginine (Table 1).

TABLE 1

Peptides of Group 1

| SEQ ID NO: | Amino acid sequence (N→C) |
|---|---|
| 1 | KYQRRKKNKY |
| 2 | KYQRRKRNKY |
| 3 | KYQRRRKNKY |
| 4 | KYQRRRRNKY |
| 5 | KYQRKKKNKY |
| 6 | KYQRKRKNKY |
| 7 | KYQRKKRNKY |
| 8 | KYQRKRRNKY |

Next, peptides of Group 2 were synthesized by substituting any amino acid at positions 5 to 7 of the peptide of SEQ ID NO: 1 with lysine or arginine or by substituting an amino acid at position 8 of the peptide of SEQ ID NO: 1 with serine (Table 2).

TABLE 2

Peptides of Group 2

| SEQ ID NO: | Amino acid sequence (N→C) |
|---|---|
| 9 | KYQRRKKSKY |
| 10 | KYQRRKRSKY |

TABLE 2-continued

Peptides of Group 2

| SEQ ID NO: | Amino acid sequence (N→C) |
|---|---|
| 11 | KYQRRRKSKY |
| 12 | KYQRRRRSKY |
| 13 | KYQRKKKSKY |
| 14 | KYQRKRKSKY |
| 15 | KYQRKKRSKY |
| 16 | KYQRKRRSKY |

Next, peptides of Group 3 were synthesized by substituting any amino acid at positions 5 to 7 of the peptide of SEQ ID NO: 1 with lysine or arginine or by substituting an amino acid at position 9 of the peptide of SEQ ID NO: 1 with tyrosine (Table 3).

TABLE 3

Peptides of Group 3

| SEQ ID NO: | Amino acid sequence (N→C) |
|---|---|
| 17 | KYQRRKKNYK |
| 18 | KYQRRKRNYK |
| 19 | KYQRRRKNYK |
| 20 | KYQRRRRNYK |
| 21 | KYQRKKKNYK |
| 22 | KYQRKRKNYK |
| 23 | KYQRKKRNYK |
| 24 | KYQRKRRNYK |

Next, peptides of Group 4 were synthesized by substituting any amino acid at positions 5 to 7 of the peptide of SEQ ID NO: 1 with lysine or arginine, by substituting an amino acid at position 8 of the peptide of SEQ ID NO: 1 with serine, by substituting an amino acid at position 9 of the peptide of SEQ ID NO: 1 with tyrosine, or by substituting an amino acid at position 10 of the peptide of SEQ ID NO: 1 with lysine (Table 4).

TABLE 4

Peptides of Group 4

| SEQ ID NO: | Amino acid sequence (N→C) |
|---|---|
| 25 | KYQRRKKSYK |
| 26 | KYQRRKRSYK |
| 27 | KYQRRRKSYK |
| 28 | KYQRRRRSYK |
| 29 | KYQRKKKSYK |
| 30 | KYQRKRKSYK |
| 31 | KYQRKKRSYK |
| 32 | KYQRKRRSYK |

Next, peptides of Group 5 were synthesized by substituting an amino acid at position 3 of the peptide of SEQ ID NO: 1 with arginine, by substituting an amino acid at position 4 of the peptide of SEQ ID NO: 1 with glutamine, or by substituting any amino acid at positions 5 to 7 of the peptide of SEQ ID NO: 1 with lysine or arginine (Table 5).

TABLE 5

Peptides of Group 5

| SEQ ID NO: | Amino acid sequence (N→C) |
|---|---|
| 33 | KYRQRKKNKY |
| 34 | KYRQRKRNKY |
| 35 | KYRQRRKNKY |
| 36 | KYRQRRRNKY |
| 37 | KYRQKKKNKY |
| 38 | KYRQKRKNKY |
| 39 | KYRQKKRNKY |
| 40 | KYRQKRRNKY |

Next, peptides of Group 6 were synthesized by substituting an amino acid at position 3 of the peptide of SEQ ID NO: 1 with arginine, by substituting an amino acid at position 4 of the peptide of SEQ ID NO: 1 with glutamine, by substituting any amino acid at positions 5 to 7 of the peptide of SEQ ID NO: 1 with lysine or arginine, or by substituting an amino acid at position 8 of the peptide of SEQ ID NO: 1 with serine (Table 6).

TABLE 6

Peptides of Group 6

| SEQ ID NO: | Amino acid sequence (N→C) |
|---|---|
| 41 | KYRQRKKSKY |
| 42 | KYRQRKRSKY |
| 43 | KYRQRRKSKY |
| 44 | KYRQRRRSKY |
| 45 | KYRQKKKSKY |
| 46 | KYRQKRKSKY |
| 47 | KYRQKKRSKY |
| 48 | KYRQKRRSKY |

Next, peptides of Group 7 were synthesized by substituting an amino acid at position 3 of the peptide of SEQ ID NO: 1 with arginine, by substituting an amino acid at position 4 of the peptide of SEQ ID NO: 1 with glutamine, by substituting any amino acid at positions 5 to 7 of the peptide of SEQ ID NO: 1 with lysine or arginine, by substituting an amino acid at position 9 of the peptide of SEQ ID NO: 1 with tyrosine, or by substituting an amino acid at position 10 of the peptide of SEQ ID NO: 1 with lysine (Table 7).

TABLE 7

Peptides of Group 7

| SEQ ID NO: | Amino acid sequence (N→C) |
|---|---|
| 49 | KYRQRKKNYK |
| 50 | KYRQRKRNYK |
| 51 | KYRQRRKNYK |
| 52 | KYRQRRRNYK |
| 53 | KYRQKKKNYK |
| 54 | KYRQKRKNYK |
| 55 | KYRQKKRNYK |
| 56 | KYRQKRRNYK |

Next, peptides of Group 8 were synthesized by substituting an amino acid at position 3 of the peptide of SEQ ID NO: 1 with arginine, by substituting an amino acid at position 4 of the peptide of SEQ ID NO: 1 with glutamine, by substituting any amino acid at positions 5 to 7 of the peptide of SEQ ID NO: 1 with lysine or arginine, by substituting an amino acid at position 8 of the peptide of SEQ ID NO: 1 with serine, by substituting an amino acid at position 9 of the peptide of SEQ ID NO: 1 with tyrosine, or by substituting an amino acid at position 10 of the peptide of SEQ ID NO: 1 with lysine (Table 8).

TABLE 8

Peptides of Group 8

| SEQ ID NO: | Amino acid sequence (N→C) |
|---|---|
| 57 | KYRQRKKSYK |
| 58 | KYRQRKRSYK |
| 59 | KYRQRRKSYK |
| 60 | KYRQRRRSYK |
| 61 | KYRQKKKSYK |
| 62 | KYRQKRKSYK |
| 63 | KYRQKKRSYK |
| 64 | KYRQKRRSYK |

Next, peptides of Group 9 were synthesized by substituting an amino acid at position 3 of the peptide of SEQ ID NO: 1 with lysine, by substituting an amino acid at position 4 of the peptide of SEQ ID NO: 1 with glutamine, or by substituting any amino acid at positions 5 to 7 of the peptide of SEQ ID NO: 1 with lysine or arginine (Table 9).

TABLE 9

Peptides of Group 9

| SEQ ID NO: | Amino acid sequence (N→C) |
|---|---|
| 65 | KYKQRKKNKY |
| 66 | KYKQRKRNKY |
| 67 | KYKQRRKNKY |
| 68 | KYKQRRRNKY |
| 69 | KYKQKKKNKY |
| 70 | KYKQKRKNKY |
| 71 | KYKQKKRNKY |
| 72 | KYKQKRRNKY |

Next, peptides of Group 10 were synthesized by substituting an amino acid at position 3 of the peptide of SEQ ID NO: 1 with lysine, by substituting an amino acid at position 4 of the peptide of SEQ ID NO: 1 with glutamine, by substituting any amino acid at positions 5 to 7 of the peptide of SEQ ID NO: 1 with lysine or arginine, or by substituting an amino acid at position 8 of the peptide of SEQ ID NO: 1 with serine (Table 10).

TABLE 10

Peptides of Group 10

| SEQ ID NO: | Amino acid sequence (N→C) |
|---|---|
| 73 | KYKQRKKSKY |
| 74 | KYKQRKRSKY |
| 75 | KYKQRRKSKY |
| 76 | KYKQRRRSKY |
| 77 | KYKQKKKSKY |
| 78 | KYKQKRKSKY |
| 79 | KYKQKKRSKY |
| 80 | KYKQKRRSKY |

Next, peptides of Group 11 were synthesized by substituting an amino acid at position 3 of the peptide of SEQ ID NO: 1 with lysine, by substituting an amino acid at position 4 of the peptide of SEQ ID NO: 1 with glutamine, by substituting any amino acid at positions 5 to 7 of the peptide of SEQ ID NO: 1 with lysine or arginine, by substituting an amino acid at position 9 of the peptide of SEQ ID NO: 1 with tyrosine, or by substituting an amino acid at position 10 of the peptide of SEQ ID NO: 1 with lysine (Table 11).

TABLE 11

Peptides of Group 11

| SEQ ID NO: | Amino acid sequence (N→C) |
|---|---|
| 81 | KYKQRKKNYK |
| 82 | KYKQRKRNYK |
| 83 | KYKQRRKNYK |

TABLE 11-continued

Peptides of Group 11

| SEQ ID NO: | Amino acid sequence (N→C) |
|---|---|
| 84 | KYKQRRRNYK |
| 85 | KYKQKKKNYK |
| 86 | KYKQKRKNYK |
| 87 | KYKQKKRNYK |
| 88 | KYKQKRRNYK |

Lastly, peptides of Group 12 were synthesized by substituting an amino acid at position 3 of the peptide of SEQ ID NO: 1 with lysine, by substituting an amino acid at position 4 of the peptide of SEQ ID NO: 1 with glutamine, by substituting any amino acid at positions 5 to 7 of the peptide of SEQ ID NO: 1 with lysine or arginine, by substituting an amino acid at position 8 of the peptide of SEQ ID NO: 1 with serine, by substituting an amino acid at position 9 of the peptide of SEQ ID NO: 1 with tyrosine, or by substituting an amino acid at position 10 of the peptide of SEQ ID NO: 1 with lysine (Table 12).

TABLE 12

Peptides of Group 12

| SEQ ID NO: | Amino acid sequence (N→C) |
|---|---|
| 89 | KYKQRKKSYK |
| 90 | KYKQRKRSYK |
| 91 | KYKQRRKSYK |
| 92 | KYKQRRRSYK |
| 93 | KYKQKKKSYK |
| 94 | KYKQKRKSYK |
| 95 | KYKQKKRSYK |
| 96 | KYKQKRRSYK |

Example 2: Verification of the Effect of Promoting Regeneration of Dentin Using the Odontoblasts Example 2-1: Validation of the Effect of Peptides on the Activity of the DSPP (Dentin Sialophosphoprotein) Promoter First, MDPC-23 cells, which are mouse-derived odontoblasts, were cultured in DMEM medium containing 10% FBS, 5% CO2 and 37° C.

Next, the cultured MDPC-23 cells were dispensed into a 24-well plate at $5 \times 10^4$ cells per well, incubated for 24 hours. And then using Lipofectamine Plus™ reagent, the cultured cells were transformed by introducing a recombinant (pGL3 vector) the DSPP promoter and luciferase gene were introduced. The transformed MDPC-23 cells were treated with the peptides of groups 1 to 12 synthesized in Example 1, respectively, and cultured for 48 hours. Then luciferase activity was measured, and the average level was compared (FIG. 1A). As a control, transformed MDPC-23 cells without an odontoblast differentiation promoting peptide were used.

FIG. 1A is a graph showing the effect of each peptide provided in the present invention on the expression of DSPP, an odontoblast differentiation marker gene, for each group. As shown in FIG. 1A, each peptide provided in the present invention showed a value of about 1.3 times or more of the luciferase activity level measured in the control group as a whole, but the difference was shown for each group, and the peptide of group 12 was the highest. And the next highest level of luciferase activity was from group 11 peptide.

Therefore, it was verified that the peptides provided by the present invention exhibit an effect of activating the DSPP promoter.

Figure 1B:
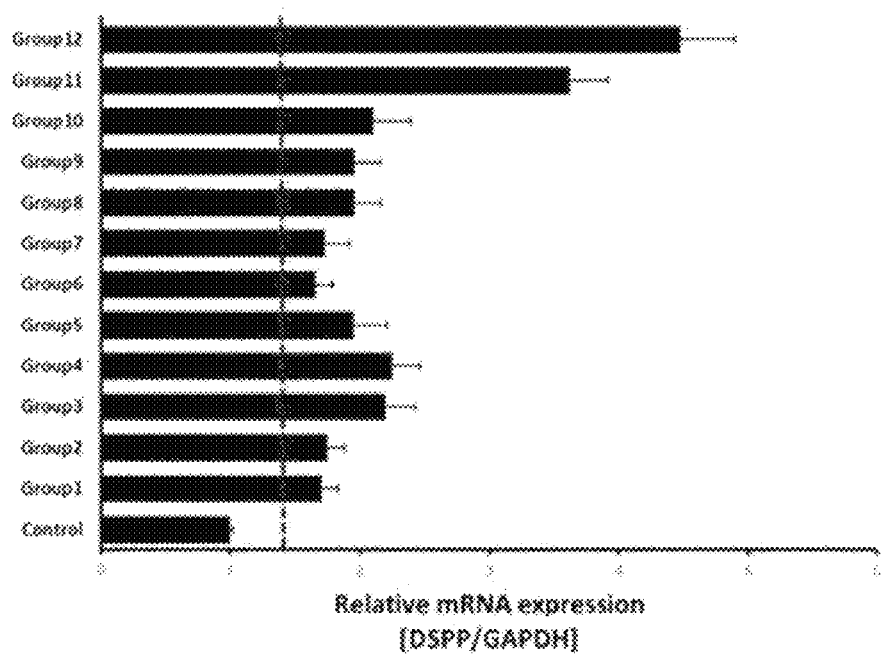
FIG. 1B is a graph showing the results of comparing the expression levels of the odontoblast differentiation marker Dspp gene in MDPC-23 cells treated with the peptides included in the toothpaste composition for alleviating dentin hyperesthesia according to an embodiment of the present invention.

Example 2-2: Verification of the Effect of Peptides on the Expression Level of the DSPP Gene, an Odontoblast Differentiation Marker Gene The MDPC-23 cells cultured in Example 2-1 were treated with the peptides of each group synthesized in Example 1, then cultured for 48 hours. The mRNA level of the DSPP, an odontoblast differentiation marker gene, expressed in the MDPC-23 cells were measured, and the measured mRNA level of each DSPP gene was converted into a relative ratio to the mRNA level of the DSPP gene measured in control (Tables 13 to 24). In addition, the average value of the mRNA level of the DSPP gene measured according to the peptides of each group was compared (FIG. 1B). At this time, as a control, MDPC-23 cells that were not treated with the peptide promoting differentiation of odontoblast were used.

The expression level of the DSPP gene was measured through RT-PCR and real-time PCR analysis: Specifically, total RNA was extracted from the MDPC-23 cells using TRIzol reagent. 2 μg of the total RNA, 1 μl of reverse transcriptase, and 0.5 μg of oligo (oligo; dT) were used to synthesize cDNA. The synthesized cDNA was used in a real-time polymerase chain reaction. The real-time polymerase chain reaction was performed on an ABI PRISM 7500 sequence detection system (Applied Biosystems) and an SYBR GREEN PCR Master Mix (Takara, Japan). The real-time polymerase chain reaction was performed under conditions of 94° C., 1 min; 95° C., 15 sec; 60° C., 34 sec for 40 cycles. Results were analyzed by a comparative cycle threshold (CT) method. At this time, the Gapdh gene was used as the internal control group, and the measured value was repeated three times. The mean value and standard deviation value thereof were used.

```
Dspp_F:
                                     (SEQ ID NO: 97)
5'-ATTCCGGTTCCCCAGTTAGTA-3'

Dspp_R:
                                     (SEQ ID NO: 98)
5'-CTGTTGCTAGTGGTGCTGTT-3'

Gapdh_F:
                                     (SEQ ID NO: 99)
5'-AGGTCGGTGTGAACGGATTTG-3'

Gapdh_R:
                                     (SEQ ID NO: 100)
5'-TGTAGACCATGTAGTTGAGGTCA-3'
```

TABLE 13

Effects of peptides of group 1 on mRNA level of Dspp gene

| SEQ ID NO: | mRNA level of Dspp gene | |
|---|---|---|
| | Mean | Standard deviation |
| 1 | 1.754 | 0.132 |
| 2 | 1.646 | 0.092 |
| 3 | 1.464 | 0.221 |
| 4 | 1.855 | 0.102 |
| 5 | 1.639 | 0.057 |
| 6 | 1.746 | 0.091 |
| 7 | 1.864 | 0.132 |
| 8 | 1.639 | 0.032 |

TABLE 14

Effects of peptides of group 2 on mRNA level of Dspp gene

| SEQ ID NO: | mRNA level of Dspp gene | |
|---|---|---|
| | Mean | Standard deviation |
| 9 | 1.854 | 0.032 |
| 10 | 1.746 | 0.052 |
| 11 | 1.639 | 0.201 |
| 12 | 1.548 | 0.027 |
| 13 | 1.685 | 0.077 |
| 14 | 1.846 | 0.141 |
| 15 | 1.964 | 0.279 |
| 16 | 1.739 | 0.092 |

TABLE 15

Effects of peptides of group 3 on mRNA level of Dspp gene

| SEQ ID NO: | mRNA level of Dspp gene | |
|---|---|---|
| | Mean | Standard deviation |
| 17 | 2.117 | 0.209 |
| 18 | 2.319 | 0.092 |
| 19 | 1.931 | 0.102 |
| 20 | 2.553 | 0.099 |
| 21 | 1.893 | 0.132 |
| 22 | 2.412 | 0.072 |
| 23 | 2.171 | 0.281 |
| 24 | 2.212 | 0.111 |

TABLE 16

Effects of peptides of group 4 on mRNA level of Dspp gene

| SEQ ID NO: | mRNA level of Dspp gene | |
|---|---|---|
| | Mean | Standard deviation |
| 25 | 2.371 | 0.089 |
| 26 | 2.193 | 0.052 |
| 27 | 1.993 | 0.202 |
| 28 | 2.453 | 0.192 |
| 29 | 1.883 | 0.101 |
| 30 | 2.512 | 0.209 |
| 31 | 2.371 | 0.139 |
| 32 | 2.219 | 0.302 |

TABLE 17

Effects of peptides of group 5 on mRNA level of Dspp gene

| SEQ ID NO: | mRNA level of Dspp gene | |
|---|---|---|
| | Mean | Standard deviation |
| 33 | 1.712 | 0.091 |
| 34 | 1.931 | 0.172 |
| 35 | 1.983 | 0.102 |
| 36 | 2.319 | 0.292 |
| 37 | 1.597 | 0.301 |
| 38 | 2.116 | 0.211 |
| 39 | 1.712 | 0.191 |
| 40 | 2.219 | 0.212 |

TABLE 18

Effects of peptides of group 6 on mRNA level of Dspp gene

| SEQ ID NO: | mRNA level of Dspp gene | |
|---|---|---|
| | Mean | Standard deviation |
| 41 | 1.546 | 0.091 |
| 42 | 1.586 | 0.103 |
| 43 | 1.669 | 0.095 |
| 44 | 1.793 | 0.203 |
| 45 | 1.532 | 0.31 |
| 46 | 1.887 | 0.077 |
| 47 | 1.697 | 0.009 |
| 48 | 1.558 | 0.201 |

TABLE 19

Effects of peptides of group 7 on mRNA level of Dspp gene

| SEQ ID NO: | mRNA level of Dspp gene | |
|---|---|---|
| | Mean | Standard deviation |
| 49 | 1.923 | 0.192 |
| 50 | 1.887 | 0.007 |
| 51 | 1.601 | 0.082 |
| 52 | 2.019 | 0.135 |
| 53 | 1.592 | 0.222 |
| 54 | 1.437 | 0.341 |
| 55 | 1.663 | 0.094 |
| 56 | 1.701 | 0.109 |

TABLE 20

Effects of peptides of group 8 on mRNA level of Dspp gene

| SEQ ID NO: | mRNA level of Dspp gene | |
|---|---|---|
| | Mean | Standard deviation |
| 57 | 2.039 | 0.082 |
| 58 | 1.998 | 0.172 |
| 59 | 1.792 | 0.007 |
| 60 | 2.107 | 0.201 |
| 61 | 2.301 | 0.019 |
| 62 | 1.672 | 0.308 |
| 63 | 1.769 | 0.085 |
| 64 | 1.967 | 0.039 |

TABLE 21

Effects of peptides of group 9 on mRNA level of Dspp gene

| SEQ ID NO: | mRNA level of Dspp gene | |
|---|---|---|
| | Mean | Standard deviation |
| 65 | 1.723 | 0.072 |
| 66 | 1.627 | 0.291 |
| 67 | 1.777 | 0.027 |
| 68 | 1.432 | 0.41 |
| 69 | 2.011 | 0.081 |
| 70 | 1.927 | 0.105 |
| 71 | 1.879 | 0.06 |
| 72 | 2.011 | 0.009 |

TABLE 22

Effects of peptides of group 10 on mRNA level of Dspp gene

| SEQ ID NO: | mRNA level of Dspp gene | |
|---|---|---|
| | Mean | Standard deviation |
| 73 | 2.035 | 0.021 |
| 74 | 2.011 | 0.063 |
| 75 | 1.997 | 0.059 |
| 76 | 2.351 | 0.109 |
| 77 | 1.729 | 0.111 |
| 78 | 2.635 | 0.091 |
| 79 | 2.231 | 0.077 |
| 80 | 1.837 | 0.201 |

TABLE 23

Effects of peptides of group 11 on mRNA level of Dspp gene

| SEQ ID NO: | mRNA level of Dspp gene | |
|---|---|---|
| | Mean | Standard deviation |
| 81 | 3.092 | 0.152 |
| 82 | 3.361 | 0.098 |
| 83 | 3.572 | 0.209 |
| 84 | 3.702 | 0.301 |
| 85 | 3.67 | 0.088 |
| 86 | 3.705 | 0.137 |
| 87 | 3.888 | 0.072 |
| 88 | 4.021 | 0.301 |

TABLE 24

Effects of peptides of group 12 on mRNA level of Dspp gene

| SEQ ID NO: | mRNA level of Dspp gene | |
|---|---|---|
| | Mean | Standard deviation |
| 89 | 4.211 | 0.413 |
| 90 | 4.811 | 0.302 |
| 91 | 4.362 | 0.182 |
| 92 | 4.211 | 0.287 |
| 93 | 4.525 | 0.25 |
| 94 | 3.836 | 0.099 |
| 95 | 4.62 | 0.401 |
| 96 | 5.211 | 0.371 |

As shown in Tables 13 to 24, compared to the mRNA level of the DSPP gene measured in the control group, it was confirmed that the mRNA levels of the DSPP gene of the experimental group treated with the peptide were all 1.3 times or more. In particular, it was confirmed that all the peptides of group 11 showed a value of 3 times or more in the mRNA level of the DSPP gene, and all peptides of group 12 showed a value of 3.8 times or more in the mRNA level of the DSPP gene.

In addition, FIG. 1B is a graph comparing the expression level of the DSPP gene, an odontoblast differentiation marker, in MDPC-23 cells treated with an odontoblast differentiation promoting peptide. As shown in FIG. 1B, when the peptide for promoting differentiation of odontoblast was treated, the mRNA level of the DSPP gene, which is a marker for odontoblast differentiation, is increased. Similar to that of FIG. 1A, it was confirmed that a value of about 1.3 times or more compared to the level of DSPP gene mRNA was measured in the control group.

Example 2-3: Verification of the Effect of the Peptide on the Expression Level of the Odontoblast Differentiation Marker Genes DSPP, Dmp1 and Nestin Genes From the results of Example 2-2, it was confirmed that the odontoblast differentiation promoting peptide could increase the mRNA level of the DSPP gene, and in particular, the peptides of groups 11 and 12 can increase the mRNA level of the DSPP gene by at least 3 times or more.

Accordingly, it was confirmed whether the peptides of groups 11 and 12 can also increase the mRNA levels of the Dmp1 and Nestin genes, which are other odontoblast differentiation marker genes.

Figure 1C:
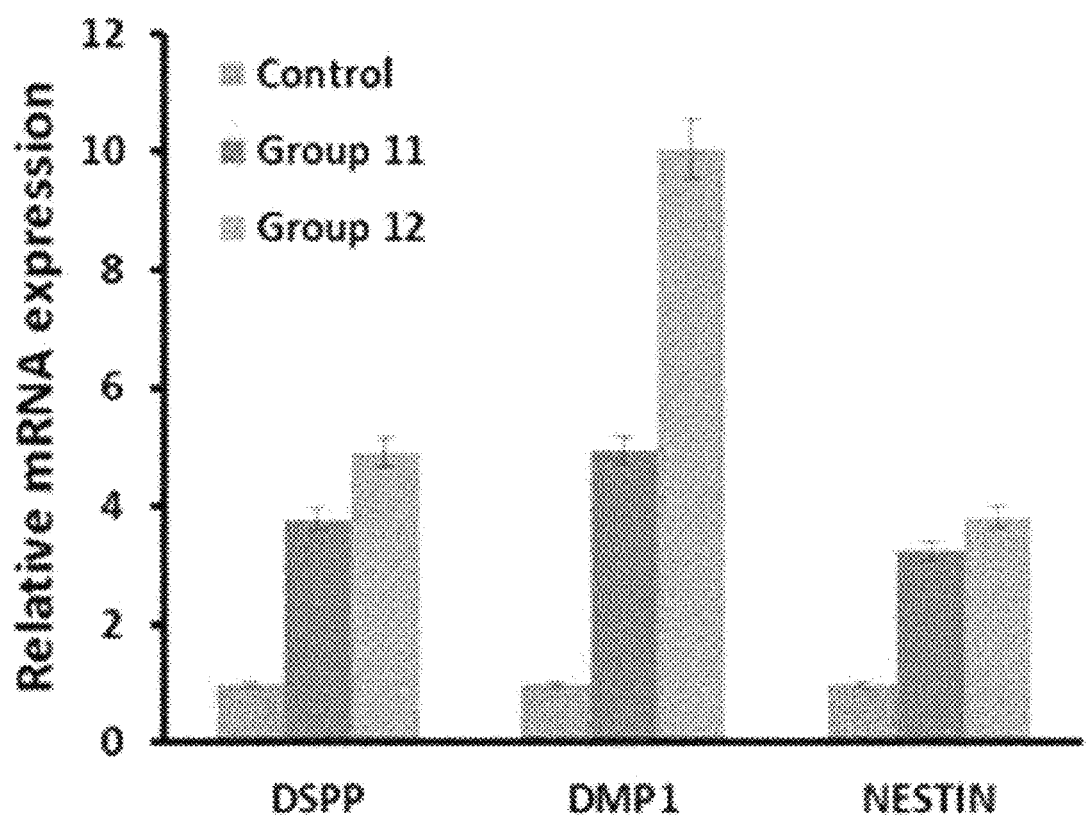
FIG. 1C is a graph showing the results of comparing expression levels of odontoblast differentiation marker genes, Dspp, Dmp1, and Nestin in MDPC-23 cells treated with peptides of Group 11 and Group 12 included in the toothpaste composition for alleviating dentin hyperesthesia according to an embodiment of the present invention.

The following primers were used with the method from Example 2-2. The peptides of groups 11 and 12 were used, thereby affecting the expression levels of Dmp1 and Nestin genes. The effect of the differentiation promoting peptide was measured, and the average level was compared (FIG. 1C). At this time, as a control group, MDPC-23 cells without a peptide promoting differentiation of odontoblast were used.

```
Dmp1_F:
                                       (SEQ ID NO 101)
5'-CATTCTCCTTGTGTTCCTTTGGG-3'

Dmp1_R:
                                       (SEQ ID NO 102)
5'-TGTGGTCACTATTTGCCTGTG-3'

Nestin_F:
                                       (SEQ ID NO 103)
5'-CCCTGAAGTCGAGGAGCTG-3'

Nestin_R:
                                       (SEQ ID NO 104)
5'-CTGCTGCACCTCTAAGCGA-3'
```

FIG. 1C is a graph showing the results of comparing the expression levels of the odontoblast differentiation marker DSPP, Dmp1, and Nestin genes in MDPC-23 cells treated with the peptides of groups 11 and 12. As shown in FIG. 1c, when the odontoblast differentiation promoting peptide was treated, the expression levels of the odontoblast differentiation marker DSPP, Dmp1, and Nestin genes were all increased, but the level of increase for each gene was different. It was confirmed that the peptide of group 12 was more effective.

Since each differentiation marker gene is known to be involved in the differentiation of odontoblasts and dentin calcification, the peptides provided in the present invention were analyzed whether they promote the dentin regeneration.

Example 2-4: Evaluation of Cytotoxicity of Peptides on Pulp Tissue Cells

Human dental pulp cells were separated from wisdom teeth of 10 adults (aged 18-22) at the School of Dentistry, Seoul National University. In detail, all experiments were performed after the approval of the Institutional Review Board and obtaining the informed consent from patients. Wisdom teeth were fractured according to a method of Jung H S et al. (J Mol Histol. (2011)) to expose the dental pulps, and dental pulp tissues were separated with forceps. Each of the separated dental pulp tissues was chopped into small pieces with a razor blade, put in a 60-mm dish, covered with a coverslip, and then cultured in a Dulbecco's modified Eagle's medium.

Figure 1D:
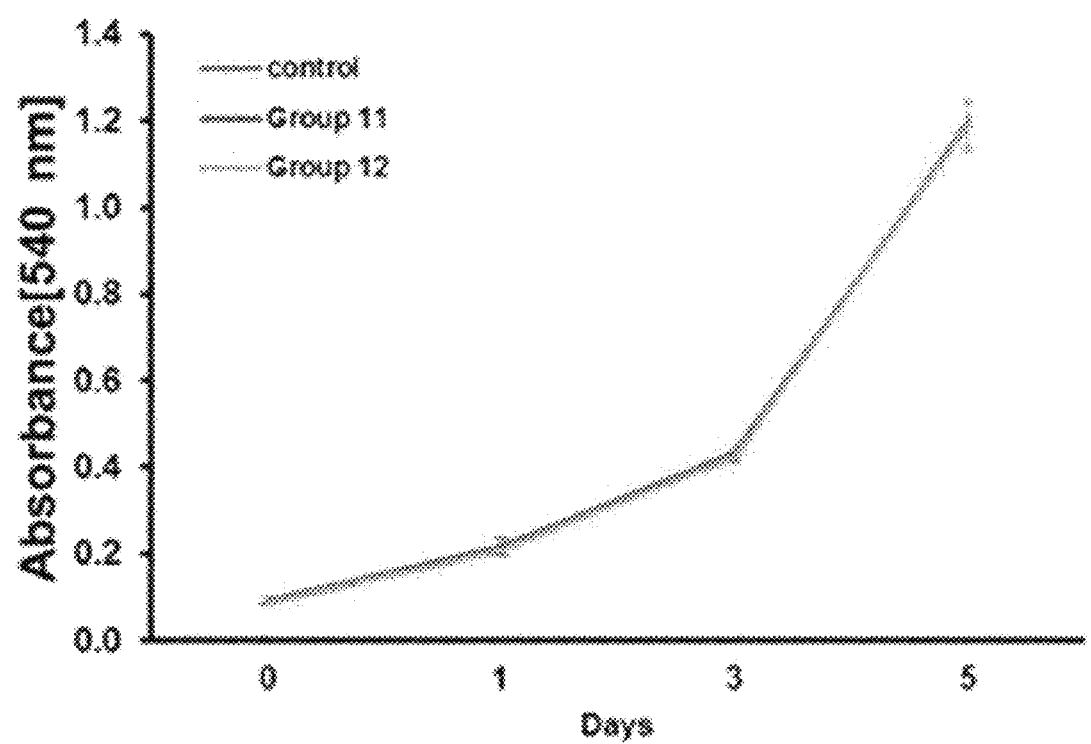
FIG. 1D is a graph showing the results of evaluating cytotoxicity of the peptides included in the toothpaste composition for alleviating dentin hyperesthesia according to an embodiment of the present invention.

Next, the obtained dental pulp tissue cells were dispensed into a 96-well plate so the number of cells per well was to be about $3 \times 10^3$, cultured for 24 hours. Then the peptides of groups 11 or 12 were treated at a concentration of 10 or 50 μg/ml. And it was incubated again for 1, 3 or 5 days. The cultured cells were washed with PBS, 20 μl of MTT solution was added, and then reacted at about 37° C. for 4 hours. After the reaction was completed, the MTT solution was removed, 100 μl of DMSO was added, and absorbance was measured at a wavelength of 540 nm (FIG. 1D). At this time, as a control, pulp tissue cells cultured without the peptide were used.

FIG. 1D is a graph showing the cytotoxicity of a peptide that promotes the differentiation of oblasts to dental pulp tissue cells. As shown in FIG. 1D, it was confirmed that the survival rate of pulp tissue cells was at the same level as that of the control group even when the odontoblast differentiation promoting peptide was added.

Example 3: Preparation of Toothpaste Composition for Alleviating Dentin Hyperesthesia Step 1
Mixing purified water and D-sorbitol solution
Step 2
Tricalcium phosphate, aminocaproic acid, allantoin, hydrous silicic acid, sodium PCA solution, hydroxyapatite, peptide (SEQ ID NO: 96), enzyme-treated *stevia*, and xylitol were added and stirred in a stirrer for about 40 minutes (stirring conditions: PADDLE 10-30 rpm, DISPERSE 500-600 rpm, HOMO 2400-3200 rpm).
Step 3
Add (concentrated) glycerin and xanthan gum and stir for about 40 minutes (Stirring condition: PADDLE 10-30 rpm, DISPERSE 500-600 rpm, HOMO 2400-3200 rpm).
Step 4:
(concentrated) Glycerin, Carboxymethyl Cellulose Sodium Salt (CMC) added and stirred for about 40 minutes (Stirring condition: PADDLE 10-30 rpm, DISPERSE 500-600 rpm, HOMO 2400-3200 rpm).
Step 5
Add sodium cocoylmethyltaurate and stirring for about 20 minutes (Stirring conditions: PADDLE 10-30 rpm, DISPERSE 450-650 rpm).
Step 6
Add green tea extract, chamomile extract, rosemary extract, myrrh tincture, rhatany tincture, chamomile tincture, mastic oil 40, propolis extract, grapefruit seed extract, spearmint, peppermint oil, and stir for about 15 minutes (stirring condition: PADDLE 10-30 rpm, DISPERSE 450-650 rpm)

In each step, stirring was carried out under reduced pressure conditions (−760 mmHg).

TABLE 25

Toothpaste composition for alleviating dentin hyperesthesia according to Example 3

| | Component | Ingredient | Content (Wt %) |
|---|---|---|---|
| 1 | Solvent | Purified water | 21.587 |
| | humectant | D-Sorbitol Solution | 30 |
| | Staple | Tricalcium phosphate | 32 |
| | | Aminocaproic acid | 0.2 |
| | | Allantoin | 2 |
| | viscosity modifier | hydrous silicic acid | 4 |
| | humectant | Sodium PCA solution | 3 |
| | diluting agent | Hydroxyapatite | 0.05 |
| | Odontoblast differentiation promoting peptide | Peptide (SEQ ID NO: 96) | 0.002 |
| | sweetening agent | enzyme-treated stevia | 0.1 |
| | | Xylitol | 0.1 |
| 2 | humectant | (concentrated) glycerin | 2 |
| | viscosity modifier | Xanthan gum | 0.3 |
| 3 | humectant | (concentrated) glycerin | 2 |
| | viscosity modifier | CMC(Carboxymethyl Cellulose Sodium Salt) | 0.6 |
| 4 | Surfactant | cocoylmethyltaurate | 1.2 |
| 5 | Flavoring agent | green tea extract | 0.01 |
| | | chamomile extract | 0.01 |
| | | rosemary extract | 0.01 |
| | | myrrh tincture | 0.01 |
| | | rhatany tincture | 0.01 |
| | | chamomile tincture | 0.01 |
| | | mastic oil 40 HF-60662 | 0.001 |
| | | propolis extract | 0.05 |
| | | grapefruit seed extract | 0.1 |
| | | spearmint B71228 | 0.05 |
| | | Peppermint oil 81689 | 0.6 |
| | | Total | 100 |

Preparing Compositions of Comparative Example

Comparative Example 3-1

Prepared purified water of the same volume as in Example 3.

Comparative Example 3-2

Among the ingredients of Example 3, all ingredients other than those that did not contain an odontoblast differentiation promoting peptide (SEQ ID NO: 96) were prepared to be contained the same.

Test Example 1

MALDI-TOF analysis of toothpaste composition for alleviating dentin hyperesthesia according to Example 3

Figure 2:
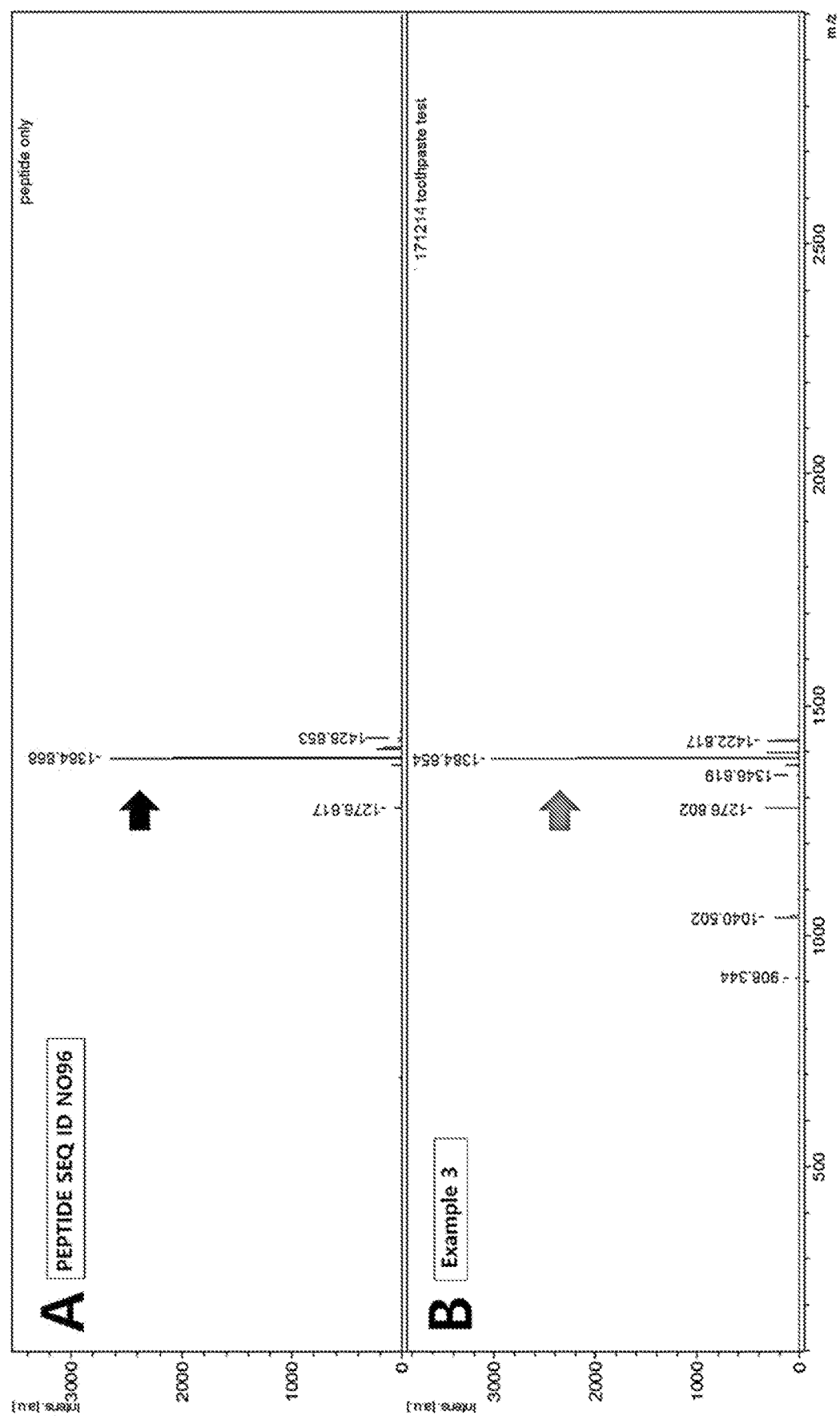
FIG. 2 is a result of measuring the molecular weight through MALDI-TOF analysis to confirm the stability of the peptide contained in the toothpaste composition for relieving dentin hyperesthesia according to an embodiment of the present invention.

A. Preparation of a toothpaste composition solution by dissolving about 0.5 g of a sample of the toothpaste composition provided in Example 3 in about 1 ml of distilled water B. Centrifuge the solution of A. at about 15,000 rpm for about 10 minutes and collect the supernatant C. 2 ul of the supernatant collected in B. was mixed with 2 ul of the substrate solution (10 mg/mL of α-Cyano-4-hydroxycinnamic acid (CHCA) in 0.1% TFA/ACN (1:1, v/v)) and MALDI-TOF analysis was performed (ULTRAFLEXIII™ TOF/TOF (Bruker Daltonics)) (FIG. 2, B).

Test Example 2

Observation of the dentinal tubule permeability of the toothpaste composition for alleviating dentin hyperesthesia according to Example 3

A. Cut the Tooth to Expose the Dentinal Tubules

Cut the crown of the extracted person's tooth horizontally with a diamond saw to expose the dentinal tubules, and then wash twice for about 5 minutes with a phosphate buffer solution B. Cleaning Amputated Tooth The previously cut tooth was reacted with 0.5 M ethylenediaminetetraacetic acid (EDTA, pH 7.4) solution for about 5 minutes and then washed twice for about 5 minutes with a phosphate buffer solution.

C. Addition of a Fluorescent Dyeing Reagent to the Toothpaste Composition for Alleviating Dentin Hyperesthesia According to Example 3

Added 0.1% of the fluorescent dyeing reagent to the toothpaste composition for alleviating dentin hyperesthesia containing the odontoblast differentiation promoting peptide (SEQ ID NO: 96), mixed well, and then brushed the cut tooth exposed to the dentinal tubules for about 1 minute.

Figure 3:
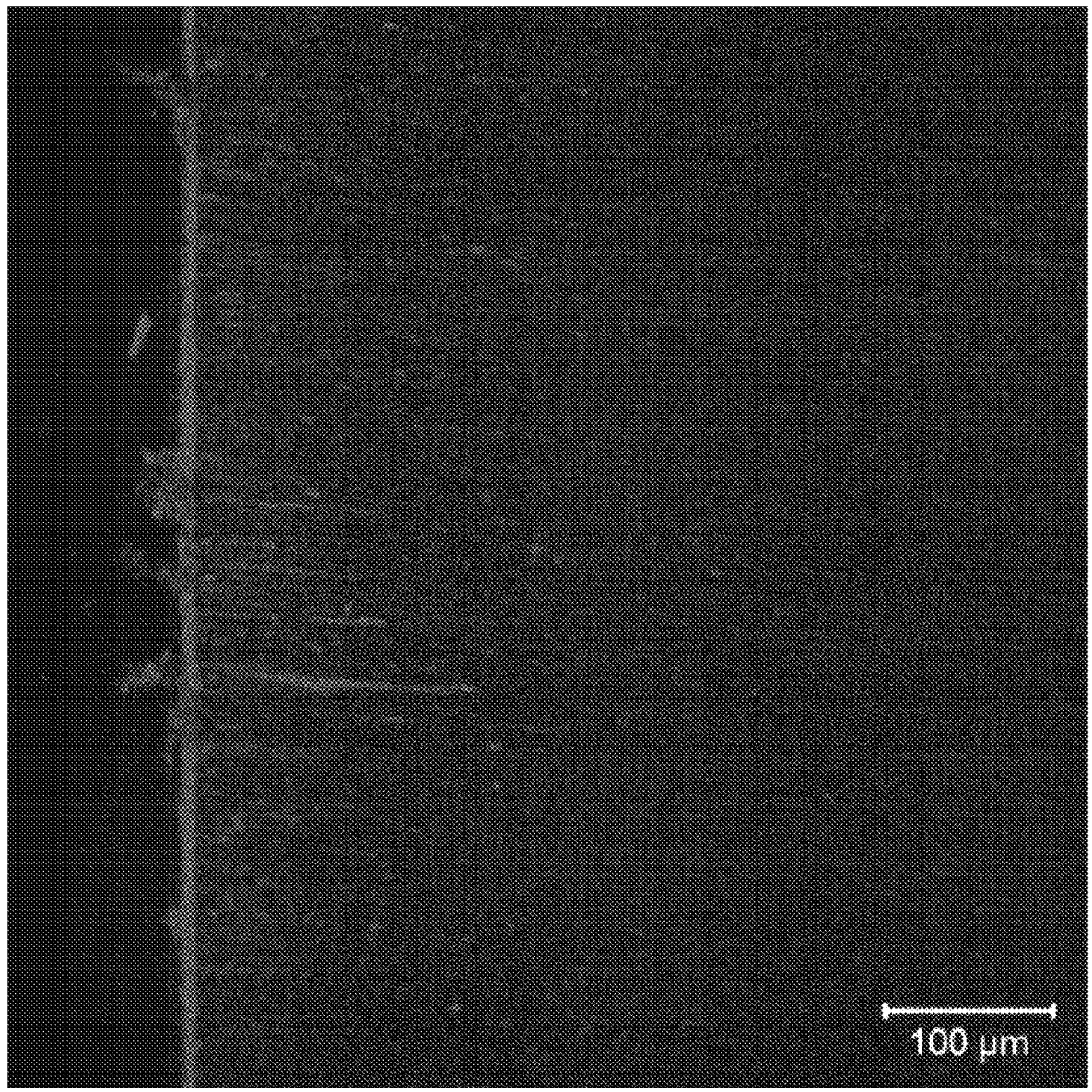
FIG. 3 shows the permeability of toothpaste composition for alleviating dentin hyperesthesia according to an embodiment of the present invention. A fluorescence dyeing reagent (Rhodamine B) was mixed and treated for 1 minute on the tooth exposed to the dentinal tubules and then observed with a fluorescence microscope.

D. Observation of Penetration of Toothpaste Composition for Alleviating Dentin Hyperesthesia The brushed cut tooth was washed 3 times with distilled water and then cut lengthwise to a thickness of about 0.5 mm so that the dentinal tubules of the cut tooth looked long using a diamond saw, and the degree of penetration was observed with a fluorescence microscope (FIG. 3)

Test Example 3

Observation of the sealing ability of the dentinal tubules of the toothpaste composition for alleviating dentin hyperesthesia according to Example 3

A. Preparation of Artificial Saliva

The composition of artificial saliva is shown in Table 26 below.

※ The purified water was added to the final concentration of each component in Table 2 and mixed, and potassium phosphate ($K_2HPO_4$) was added last.

※ The pH of artificial saliva is measured near 7.2, similar to human saliva.

TABLE 26

| Ingredient | concentration (mM) |
|---|---|
| $CaCl_2$ | 0.7 |
| $Mgcl_2$ | 0.2 |
| $K_2HPO_4$ | 4 |
| KCl | 30 |
| $NaN_3$ | 0.3 |
| HEPES | 20 |

B. Making Dentinal Tubule Specimens

The extracted human tooth was cut horizontally using a diamond saw to make a 1 mm thick, dentin specimen with exposed dentinal tubules.

※ The dentin specimen was reacted for about 5 minutes in a 32% phosphoric acid solution to expose the dentinal tubules completely, and then washed three times with purified water for about 5 minutes. Then, the dentin specimen was washed 6 times in an ultrasonic cleaner for about 5 minutes to expose the dentinal tubules completely.

Thereafter, washed three times with a phosphate buffer solution and stored.

C. Observation of the Sealing Ability of the Dentinal Tubules of the Toothpaste Composition for Alleviating Dentin Hyperesthesia Using the toothpaste composition for alleviating dentin hyperesthesia according to Example 3, the specimen was brushed for about 1 minute to the dentinal tubule specimen, washed 3 times with distilled water, and then reacted to the artificial saliva for about 24 hours.

Figure 4:
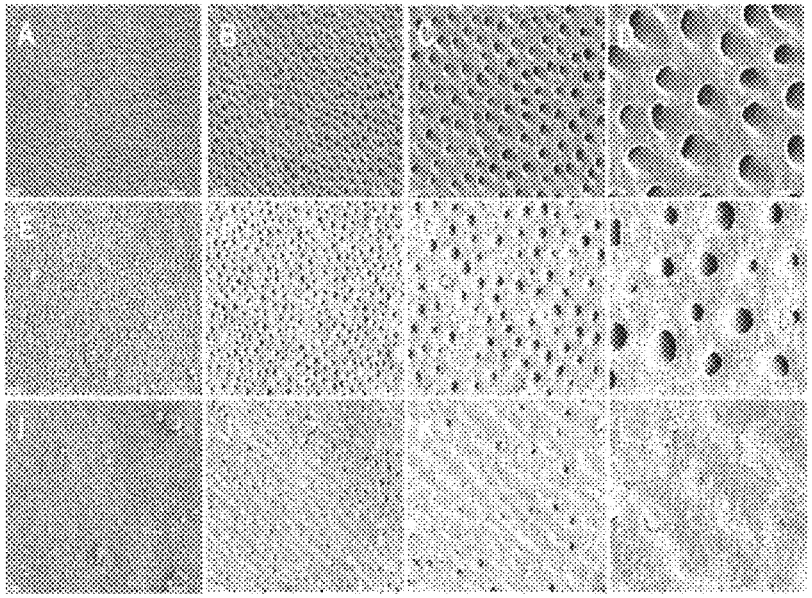
FIG. 4 shows the results of comparing the sealing ability of the dentinal tubule with the toothpaste composition for alleviating dentin hyperesthesia according to the embodiment of the present invention (example 3), comparative test example 3-1, and comparative test example 3-2.

After repeating this process for 2 weeks, washed three times with distilled water, dried, and observed the degree of dentinal tubule blockade with a scanning electron microscope (S-4700™, HITACHI, Tokyo, Japan) (FIG. 4, I-L).

Comparative Test Example 3-1

Using the purified water prepared in Comparative Example 3-1, brushed the dentinal tubule specimen for about 1 minute, washed 3 times with distilled water, and then reacted for about 24 hours in artificial saliva.

After repeating this process for 2 weeks, the specimens were washed with distilled water 3 times, dried, and observed the degree of dentinal tubule blockade with a scanning electron microscope (FIG. 4, A-D).

Comparative Test Example 3-2

Using the toothpaste prepared in Comparative Example 3-1, brushed the dentinal tubule specimen for about 1 minute, washed 3 times with distilled water, and then reacted for about 24 hours in artificial saliva.

After repeating this process for 2 weeks, the specimens were washed with distilled water 3 times, dried, and observed the degree of dentinal tubule blockade with a scanning electron microscope (FIG. 4, E-H).

Through Test Example 1, the stability of the peptide contained in the toothpaste composition for alleviating dentin hyperesthesia according to the embodiment of the present invention can be confirmed. FIG. 2 is a result of measuring the molecular weight through MALDI-TOF analysis to confirm the stability of the peptide contained in the toothpaste composition for alleviating dentin hyperesthesia according to an embodiment of the present invention. In FIG. 2, A shows the molecular weight of the peptide itself contained in the toothpaste composition for alleviating dentin hyperesthesia according to an embodiment of the present invention. In FIG. 2, B shows the molecular weight of the peptide contained in the state of the toothpaste composition for alleviating dentin hyperesthesia according to an embodiment of the present invention.

Referring to FIG. 2, it was observed that the peptide contained in the toothpaste composition according to Example 3 had the same peak (molecular weight of about 1384 Da) as the measured value of the molecular weight, and through this, the stability of mixed dentin differentiation promoting peptide in the toothpaste composition was confirmed (see graph B of FIG. 2).

According to Test Example 2, as a result of observing the dentinal tubule permeability of the toothpaste composition for alleviating dentin hyperesthesia according to Example 3 with a fluorescence microscope, as shown in FIG. 3, in the case of the tooth treated with the composition, fluorescence was strongly observed on the dentin surface. In addition, penetration of the fluorescent staining reagent was observed along the lower side of the exposed dentinal tubules.

Next, the results of comparing Test Example 3 and Comparative Test Examples 3-1 and 3-2 are as shown in FIG. 4. FIG. 4 is a set of images comparing the sealing ability of the dentinal tubules of toothpaste composition for alleviating dentin hyperesthesia according to Example 3, Comparative Example 3-1, and Comparative Example 3-2. And in more detail, A-D shows the dentinal tubules of the dentin treated only with purified water (Comparative Example 3-1), and E-H shows the toothpaste composition without odontoblast differentiation promoting peptide (Comparative Example 3-2), and I-L shows the dentinal tubules reacted with the composition, including a peptide for oral care that prevents or alleviates dentin hyperesthesia according to an embodiment of the present invention. One (size bar: A, E, I, 100 μm; B, F, J, 20 μm; C, G, K, 20 μm; D, H, L, 10 μm).

As can be seen from FIG. 4, it could be observed that the dentinal tubules were blocked by remineralization in the dentinal tubules by reacting with the toothpaste composition for alleviating dentin hyperesthesia according to an embodiment of the present invention.

FIG. 4 is an enlarged image of the dentinal tubules blocked by the composition including a peptide for oral care that prevents or alleviates dentin hyperesthesia according to an embodiment of the present invention and shows the results of remineralization in the blocked dentinal tubules and dentin surfaces.

As above, the toothpaste composition for alleviating dentin hyperesthesia according to an embodiment of the present invention forms a thin film on the dentin and at the same time strongly binds to the phosphate-calcium ions released from tricalcium phosphate, and remineralizes the exposed dentinal tubules and dentin surfaces. In other words, the toothpaste composition for alleviating dentin hyperesthesia according to an embodiment of the present invention induces remineralization not only on the surface of the exposed dentinal tubules but also inside the dentinal tubule, thereby exhibiting the effect of alleviating and/or preventing dentin hyperesthesia.

While one or more embodiments of the present invention have been described with reference to the figures, it will be understood by those of ordinary skill in the art that various changes in form and details may be made therein without departing from the spirit and scope of the present invention.

This study was supported by the technology development project of the Ministry of SMEs and Startups in 2017 [S2462696].

The invention claimed is:

1. A toothpaste composition for alleviating dentin hyperesthesia, comprising a peptide consisting of an amino acid sequence of the following Formula 1:

K-Y-R1-R2-R3-R4-R5-R6-R7-R8       (Formula 1)

wherein R1 is arginine (R), lysine (K) or glutamine (Q);
R2 is arginine (R) or glutamine (Q);
R3, R4, and R5 are arginine (R) or lysine (K), respectively;
R6 is asparagine (N) or serine (S); and
R7 and R8 are lysine (K) or tyrosine (Y), respectively,
wherein said toothpaste composition includes 0.0015-0.0025 parts by weight of the peptide, 31.00-33.00 parts by weight of tricalcium phosphate, 0.045-0.055 parts by weight of hydroxyapatite, and 20-22 parts by weight of purified water,
wherein said toothpaste composition forms a thin film on the surface of said dentin and induces remineralization on said surface of said dentin and dentinal tubule by binding with the phosphate-calcium ions released from said tricalcium phosphate.

2. The composition of claim 1, wherein said peptide is any one amino acid sequence of SEQ ID NOS: 1 to 96.

3. The composition of claim 1, wherein said toothpaste composition comprises a humectant 33-37 parts by weight, a viscosity modifier 4.4-5.4 parts by weight, a surfactant 1.1-1.3 parts by weight, and a flavoring agent 0.8-0.9 parts by weight, based on 100 parts by weight.

4. The composition of claim 1, wherein said toothpaste composition comprises 0.15-0.25 parts by weight of aminocaproic acid and 1.9-2.1 parts by weight of allantoin, based on 100 parts by weight.

5. The composition of claim 3, wherein said humectant is D-sorbitol solution, sodium PCA solution, concentrated glycerin, or a mixture thereof, wherein
said viscosity modifier is hydrous silicic acid, xanthan gum, CMC (Carboxymethyl Cellulose Sodium Salt) or a mixture thereof,
said surfactant is sodium cocoylmethyltaurate,
said flavoring agent is green tea extract, chamomile extract, rosemary extract, myrrh tincture, rhatany tincture, chamomile tincture, mastic oil 40 HF-60662, propolis extract, grapefruit seed extract, spearmint B71228, peppermint oil 81689, or a mixture thereof.

6. The composition of claim 5, wherein said humectant comprises 80-83% by weight of said D-sorbitol solution, 7-8% by weight of said Sodium PCA solution, and 10-12% by weight of said concentrated glycerin.

7. The composition of claim 5, wherein said viscosity modifier comprises 79-85% by weight of said hydrous silicic acid, 4-8% by weight of said xanthan gum, and 11-13% by weight of said CMC.

8. A method of alleviating dentin hyperesthesia in a subject in need thereof, administering the toothpaste composition according to claim 1, to dentin surface of said subject.

* * * * *

SEQUENCE LISTING

```
<160> NUMBER OF SEQ ID NOS: 104

<210> SEQ ID NO 1
<211> LENGTH: 10
<212> TYPE: PRT
<213> ORGANISM: Artificial Sequence
<220> FEATURE:
<223> OTHER INFORMATION: Novel peptide

<400> SEQUENCE: 1

Lys Tyr Gln Arg Arg Lys Lys Asn Lys Tyr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Novel peptide

<400> SEQUENCE: 2

Lys Tyr Gln Arg Arg Lys Arg Asn Lys Tyr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Novel peptide

<400> SEQUENCE: 3

Lys Tyr Gln Arg Arg Arg Lys Asn Lys Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Novel peptide

<400> SEQUENCE: 4
```

Lys Tyr Gln Arg Arg Arg Arg Asn Lys Tyr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Novel peptide

<400> SEQUENCE: 5

Lys Tyr Gln Arg Lys Lys Lys Asn Lys Tyr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Novel peptide

<400> SEQUENCE: 6

Lys Tyr Gln Arg Lys Arg Lys Asn Lys Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Novel peptide

<400> SEQUENCE: 7

Lys Tyr Gln Arg Lys Lys Arg Asn Lys Tyr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Novel peptide

<400> SEQUENCE: 8

Lys Tyr Gln Arg Lys Arg Arg Asn Lys Tyr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Novel peptide

<400> SEQUENCE: 9

Lys Tyr Gln Arg Arg Lys Lys Ser Lys Tyr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Novel peptide

<400> SEQUENCE: 10

Lys Tyr Gln Arg Arg Lys Arg Ser Lys Tyr
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Novel peptide

<400> SEQUENCE: 11

Lys Tyr Gln Arg Arg Arg Lys Ser Lys Tyr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Novel peptide

<400> SEQUENCE: 12

Lys Tyr Gln Arg Arg Arg Arg Ser Lys Tyr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Novel peptide

<400> SEQUENCE: 13

Lys Tyr Gln Arg Lys Lys Lys Ser Lys Tyr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Novel peptide

<400> SEQUENCE: 14

Lys Tyr Gln Arg Lys Arg Lys Ser Lys Tyr
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Novel peptide

<400> SEQUENCE: 15

Lys Tyr Gln Arg Lys Lys Arg Ser Lys Tyr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Novel peptide

<400> SEQUENCE: 16

Lys Tyr Gln Arg Lys Arg Arg Ser Lys Tyr

```
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Novel peptide

<400> SEQUENCE: 17

Lys Tyr Gln Arg Arg Lys Lys Asn Tyr Lys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Novel peptide

<400> SEQUENCE: 18

Lys Tyr Gln Arg Arg Lys Arg Asn Tyr Lys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Novel peptide

<400> SEQUENCE: 19

Lys Tyr Gln Arg Arg Arg Lys Asn Tyr Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Novel peptide

<400> SEQUENCE: 20

Lys Tyr Gln Arg Arg Arg Arg Asn Tyr Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Novel peptide

<400> SEQUENCE: 21

Lys Tyr Gln Arg Lys Lys Lys Asn Tyr Lys
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Novel peptide

<400> SEQUENCE: 22

Lys Tyr Gln Arg Lys Arg Lys Asn Tyr Lys
1               5                   10
```

```
<210> SEQ ID NO 23
<211> LENGTH: 10
<212> TYPE: PRT
<213> ORGANISM: Artificial Sequence
<220> FEATURE:
<223> OTHER INFORMATION: Novel peptide

<400> SEQUENCE: 23

Lys Tyr Gln Arg Lys Lys Arg Asn Tyr Lys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Novel peptide

<400> SEQUENCE: 24

Lys Tyr Gln Arg Lys Arg Arg Asn Tyr Lys
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Novel peptide

<400> SEQUENCE: 25

Lys Tyr Gln Arg Arg Lys Lys Ser Tyr Lys
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Novel peptide

<400> SEQUENCE: 26

Lys Tyr Gln Arg Arg Lys Arg Ser Tyr Lys
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Novel peptide

<400> SEQUENCE: 27

Lys Tyr Gln Arg Arg Arg Lys Ser Tyr Lys
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Novel peptide

<400> SEQUENCE: 28

Lys Tyr Gln Arg Arg Arg Arg Ser Tyr Lys
1               5                   10
```

<210> SEQ ID NO 29
<211> LENGTH: 10
<212> TYPE: PRT
<213> ORGANISM: Artificial Sequence
<220> FEATURE:
<223> OTHER INFORMATION: Novel peptide

<400> SEQUENCE: 29

Lys Tyr Gln Arg Lys Lys Lys Ser Tyr Lys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Novel peptide

<400> SEQUENCE: 30

Lys Tyr Gln Arg Lys Arg Lys Ser Tyr Lys
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Novel peptide

<400> SEQUENCE: 31

Lys Tyr Gln Arg Lys Lys Arg Ser Tyr Lys
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Novel peptide

<400> SEQUENCE: 32

Lys Tyr Gln Arg Lys Arg Arg Ser Tyr Lys
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Novel peptide

<400> SEQUENCE: 33

Lys Tyr Arg Gln Arg Lys Lys Asn Lys Tyr
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Novel peptide

<400> SEQUENCE: 34

Lys Tyr Arg Gln Arg Lys Arg Asn Lys Tyr
1               5                   10

```
<210> SEQ ID NO 35
<211> LENGTH: 10
<212> TYPE: PRT
<213> ORGANISM: Artificial Sequence
<220> FEATURE:
<223> OTHER INFORMATION: Novel peptide

<400> SEQUENCE: 35

Lys Tyr Arg Gln Arg Arg Lys Asn Lys Tyr
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Novel peptide

<400> SEQUENCE: 36

Lys Tyr Arg Gln Arg Arg Arg Asn Lys Tyr
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Novel peptide

<400> SEQUENCE: 37

Lys Tyr Arg Gln Lys Lys Lys Asn Lys Tyr
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Novel peptide

<400> SEQUENCE: 38

Lys Tyr Arg Gln Lys Arg Lys Asn Lys Tyr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Novel peptide

<400> SEQUENCE: 39

Lys Tyr Arg Gln Lys Lys Arg Asn Lys Tyr
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Novel peptide

<400> SEQUENCE: 40

Lys Tyr Arg Gln Lys Arg Arg Asn Lys Tyr
1               5                   10

<210> SEQ ID NO 41
```

```
<211> LENGTH: 10
<212> TYPE: PRT
<213> ORGANISM: Artificial Sequence
<220> FEATURE:
<223> OTHER INFORMATION: Novel peptide

<400> SEQUENCE: 41

Lys Tyr Arg Gln Arg Lys Lys Ser Lys Tyr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Novel peptide

<400> SEQUENCE: 42

Lys Tyr Arg Gln Arg Lys Arg Ser Lys Tyr
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Novel peptide

<400> SEQUENCE: 43

Lys Tyr Arg Gln Arg Arg Lys Ser Lys Tyr
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Novel peptide

<400> SEQUENCE: 44

Lys Tyr Arg Gln Arg Arg Arg Ser Lys Tyr
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Novel peptide

<400> SEQUENCE: 45

Lys Tyr Arg Gln Lys Lys Lys Ser Lys Tyr
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Novel peptide

<400> SEQUENCE: 46

Lys Tyr Arg Gln Lys Arg Lys Ser Lys Tyr
1               5                   10

<210> SEQ ID NO 47
<211> LENGTH: 10
```

```
<212> TYPE: PRT
<213> ORGANISM: Artificial Sequence
<220> FEATURE:
<223> OTHER INFORMATION: Novel peptide

<400> SEQUENCE: 47

Lys Tyr Arg Gln Lys Lys Arg Ser Lys Tyr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Novel peptide

<400> SEQUENCE: 48

Lys Tyr Arg Gln Lys Arg Arg Ser Lys Tyr
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Novel peptide

<400> SEQUENCE: 49

Lys Tyr Arg Gln Arg Lys Lys Asn Tyr Lys
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Novel peptide

<400> SEQUENCE: 50

Lys Tyr Arg Gln Arg Lys Arg Asn Tyr Lys
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Novel peptide

<400> SEQUENCE: 51

Lys Tyr Arg Gln Arg Arg Lys Asn Tyr Lys
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Novel peptide

<400> SEQUENCE: 52

Lys Tyr Arg Gln Arg Arg Arg Asn Tyr Lys
1               5                   10

<210> SEQ ID NO 53
<211> LENGTH: 10
<212> TYPE: PRT
```

<213> ORGANISM: Artificial Sequence
<220> FEATURE:
<223> OTHER INFORMATION: Novel peptide

<400> SEQUENCE: 53

Lys Tyr Arg Gln Lys Lys Lys Asn Tyr Lys
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Novel peptide

<400> SEQUENCE: 54

Lys Tyr Arg Gln Lys Arg Lys Asn Tyr Lys
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Novel peptide

<400> SEQUENCE: 55

Lys Tyr Arg Gln Lys Lys Arg Asn Tyr Lys
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Novel peptide

<400> SEQUENCE: 56

Lys Tyr Arg Gln Lys Arg Arg Asn Tyr Lys
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Novel peptide

<400> SEQUENCE: 57

Lys Tyr Arg Gln Arg Lys Lys Ser Tyr Lys
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Novel peptide

<400> SEQUENCE: 58

Lys Tyr Arg Gln Arg Lys Arg Ser Tyr Lys
1               5                   10

<210> SEQ ID NO 59
<211> LENGTH: 10
<212> TYPE: PRT
<213> ORGANISM: Artificial Sequence

```
<220> FEATURE:
<223> OTHER INFORMATION: Novel peptide

<400> SEQUENCE: 59

Lys Tyr Arg Gln Arg Arg Lys Ser Tyr Lys
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Novel peptide

<400> SEQUENCE: 60

Lys Tyr Arg Gln Arg Arg Arg Ser Tyr Lys
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Novel peptide

<400> SEQUENCE: 61

Lys Tyr Arg Gln Lys Lys Lys Ser Tyr Lys
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Novel peptide

<400> SEQUENCE: 62

Lys Tyr Arg Gln Lys Arg Lys Ser Tyr Lys
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Novel peptide

<400> SEQUENCE: 63

Lys Tyr Arg Gln Lys Lys Arg Ser Tyr Lys
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Novel peptide

<400> SEQUENCE: 64

Lys Tyr Arg Gln Lys Arg Arg Ser Tyr Lys
1               5                   10

<210> SEQ ID NO 65
<211> LENGTH: 10
<212> TYPE: PRT
<213> ORGANISM: Artificial Sequence
<220> FEATURE:
```

<223> OTHER INFORMATION: Novel peptide

<400> SEQUENCE: 65

Lys Tyr Lys Gln Arg Lys Asn Lys Tyr
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Novel peptide

<400> SEQUENCE: 66

Lys Tyr Lys Gln Arg Lys Arg Asn Lys Tyr
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Novel peptide

<400> SEQUENCE: 67

Lys Tyr Lys Gln Arg Arg Lys Asn Lys Tyr
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Novel peptide

<400> SEQUENCE: 68

Lys Tyr Lys Gln Arg Arg Arg Asn Lys Tyr
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Novel peptide

<400> SEQUENCE: 69

Lys Tyr Lys Gln Lys Lys Lys Asn Lys Tyr
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Novel peptide

<400> SEQUENCE: 70

Lys Tyr Lys Gln Lys Arg Lys Asn Lys Tyr
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Novel peptide

<400> SEQUENCE: 71

Lys Tyr Lys Gln Lys Lys Arg Asn Lys Tyr
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Novel peptide

<400> SEQUENCE: 72

Lys Tyr Lys Gln Lys Arg Arg Asn Lys Tyr
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Novel peptide

<400> SEQUENCE: 73

Lys Tyr Lys Gln Arg Lys Lys Ser Lys Tyr
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Novel peptide

<400> SEQUENCE: 74

Lys Tyr Lys Gln Arg Lys Arg Ser Lys Tyr
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Novel peptide

<400> SEQUENCE: 75

Lys Tyr Lys Gln Arg Arg Lys Ser Lys Tyr
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Novel peptide

<400> SEQUENCE: 76

Lys Tyr Lys Gln Arg Arg Arg Ser Lys Tyr
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Novel peptide

```
<400> SEQUENCE: 77

Lys Tyr Lys Gln Lys Lys Ser Lys Tyr
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Novel peptide

<400> SEQUENCE: 78

Lys Tyr Lys Gln Lys Arg Lys Ser Lys Tyr
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Novel peptide

<400> SEQUENCE: 79

Lys Tyr Lys Gln Lys Lys Arg Ser Lys Tyr
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Novel peptide

<400> SEQUENCE: 80

Lys Tyr Lys Gln Lys Arg Arg Ser Lys Tyr
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Novel peptide

<400> SEQUENCE: 81

Lys Tyr Lys Gln Arg Lys Lys Asn Tyr Lys
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Novel peptide

<400> SEQUENCE: 82

Lys Tyr Lys Gln Arg Lys Arg Asn Tyr Lys
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Novel peptide

<400> SEQUENCE: 83
```

Lys Tyr Lys Gln Arg Arg Lys Asn Tyr Lys
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Novel peptide

<400> SEQUENCE: 84

Lys Tyr Lys Gln Arg Arg Arg Asn Tyr Lys
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Novel peptide

<400> SEQUENCE: 85

Lys Tyr Lys Gln Lys Lys Lys Asn Tyr Lys
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Novel peptide

<400> SEQUENCE: 86

Lys Tyr Lys Gln Lys Arg Lys Asn Tyr Lys
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Novel peptide

<400> SEQUENCE: 87

Lys Tyr Lys Gln Lys Lys Arg Asn Tyr Lys
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Novel peptide

<400> SEQUENCE: 88

Lys Tyr Lys Gln Lys Arg Arg Asn Tyr Lys
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Novel peptide

<400> SEQUENCE: 89

```
Lys Tyr Lys Gln Arg Lys Ser Tyr Lys
1               5                   10
```

<210> SEQ ID NO 90
<211> LENGTH: 10
<212> TYPE: PRT
<213> ORGANISM: Artificial Sequence
<220> FEATURE:
<223> OTHER INFORMATION: Novel peptide

<400> SEQUENCE: 90

```
Lys Tyr Lys Gln Arg Lys Arg Ser Tyr Lys
1               5                   10
```

<210> SEQ ID NO 91
<211> LENGTH: 10
<212> TYPE: PRT
<213> ORGANISM: Artificial Sequence
<220> FEATURE:
<223> OTHER INFORMATION: Novel peptide

<400> SEQUENCE: 91

```
Lys Tyr Lys Gln Arg Arg Lys Ser Tyr Lys
1               5                   10
```

<210> SEQ ID NO 92
<211> LENGTH: 10
<212> TYPE: PRT
<213> ORGANISM: Artificial Sequence
<220> FEATURE:
<223> OTHER INFORMATION: Novel peptide

<400> SEQUENCE: 92

```
Lys Tyr Lys Gln Arg Arg Arg Ser Tyr Lys
1               5                   10
```

<210> SEQ ID NO 93
<211> LENGTH: 10
<212> TYPE: PRT
<213> ORGANISM: Artificial Sequence
<220> FEATURE:
<223> OTHER INFORMATION: Novel peptide

<400> SEQUENCE: 93

```
Lys Tyr Lys Gln Lys Lys Lys Ser Tyr Lys
1               5                   10
```

<210> SEQ ID NO 94
<211> LENGTH: 10
<212> TYPE: PRT
<213> ORGANISM: Artificial Sequence
<220> FEATURE:
<223> OTHER INFORMATION: Novel peptide

<400> SEQUENCE: 94

```
Lys Tyr Lys Gln Lys Arg Lys Ser Tyr Lys
1               5                   10
```

<210> SEQ ID NO 95
<211> LENGTH: 10
<212> TYPE: PRT
<213> ORGANISM: Artificial Sequence
<220> FEATURE:
<223> OTHER INFORMATION: Novel peptide

<400> SEQUENCE: 95

```
Lys Tyr Lys Gln Lys Lys Arg Ser Tyr Lys
```

<210> SEQ ID NO 96
<211> LENGTH: 10
<212> TYPE: PRT
<213> ORGANISM: Artificial Sequence
<220> FEATURE:
<223> OTHER INFORMATION: Novel peptide

<400> SEQUENCE: 96

Lys Tyr Lys Gln Lys Arg Arg Ser Tyr Lys
1               5                   10

<210> SEQ ID NO 97
<211> LENGTH: 21
<212> TYPE: DNA
<213> ORGANISM: Artificial Sequence
<220> FEATURE:
<223> OTHER INFORMATION: primer

<400> SEQUENCE: 97
attccggttc cccagttagt a                                         21

<210> SEQ ID NO 98
<211> LENGTH: 20
<212> TYPE: DNA
<213> ORGANISM: Artificial Sequence
<220> FEATURE:
<223> OTHER INFORMATION: primer

<400> SEQUENCE: 98
ctgttgctag tggtgctgtt                                           20

<210> SEQ ID NO 99
<211> LENGTH: 21
<212> TYPE: DNA
<213> ORGANISM: Artificial Sequence
<220> FEATURE:
<223> OTHER INFORMATION: primer

<400> SEQUENCE: 99
aggtcggtgt gaacggattt g                                         21

<210> SEQ ID NO 100
<211> LENGTH: 23
<212> TYPE: DNA
<213> ORGANISM: Artificial Sequence
<220> FEATURE:
<223> OTHER INFORMATION: primer

<400> SEQUENCE: 100
tgtagaccat gtagttgagg tca                                       23

<210> SEQ ID NO 101
<211> LENGTH: 23
<212> TYPE: DNA
<213> ORGANISM: Artificial Sequence
<220> FEATURE:
<223> OTHER INFORMATION: primer

<400> SEQUENCE: 101
cattctcctt gtgttccttt ggg                                       23

<210> SEQ ID NO 102
<211> LENGTH: 21
<212> TYPE: DNA

```
<213> ORGANISM: Artificial Sequence
<220> FEATURE:
<223> OTHER INFORMATION: primer

<400> SEQUENCE: 102
tgtggtcact atttgcctgt g                                              21

<210> SEQ ID NO 103
<211> LENGTH: 19
<212> TYPE: DNA
<213> ORGANISM: Artificial Sequence
<220> FEATURE:
<223> OTHER INFORMATION: primer

<400> SEQUENCE: 103
ccctgaagtc gaggagctg                                                 19

<210> SEQ ID NO 104
<211> LENGTH: 19
<212> TYPE: DNA
<213> ORGANISM: Artificial Sequence
<220> FEATURE:
<223> OTHER INFORMATION: primer

<400> SEQUENCE: 104
ctgctgcacc tctaagcga                                                 19
```